United States Patent [19]

Spencer

[11] Patent Number: 5,300,290

[45] Date of Patent: Apr. 5, 1994

[54] POLYMERIC PARTICLES FOR DENTAL APPLICATIONS

[75] Inventor: Jean L. Spencer, Boston, Mass.

[73] Assignee: Gillette Canada, Inc., Kirkland, Canada

[21] Appl. No.: 13,557

[22] Filed: Feb. 8, 1993

Related U.S. Application Data

[63] Continuation of Ser. No. 759,535, Sep. 13, 1991, abandoned.

[51] Int. Cl.$^5$ .................. A61K 7/16; A61K 7/22; A61K 9/14
[52] U.S. Cl. .......................... 424/54; 15/104.93; 15/167.1; 15/207.2; 132/321; 132/329; 424/401; 424/417; 424/419; 424/489; 424/490; 424/497
[58] Field of Search .............. 424/54, 401, 417, 419, 424/489, 490, 497

[56] References Cited

U.S. PATENT DOCUMENTS

| | | |
|---|---|---|
| 2,558,992 | 7/1951 | Stott . |
| 3,258,805 | 7/1966 | Rossnan . |
| 3,325,368 | 6/1967 | Wood .................... 167/93 |
| 3,542,519 | 11/1970 | Muntalto . |
| 3,810,479 | 5/1974 | Miles . |
| 3,934,001 | 1/1976 | Watson . |
| 3,956,480 | 5/1976 | Dichter et al. .................. 424/54 |
| 3,957,964 | 5/1976 | Grimm .................... 424/10 |
| 3,959,457 | 5/1976 | Speaker et al. .................. 424/19 |
| 3,978,206 | 8/1976 | Naumann et al. . |
| 4,102,992 | 7/1978 | Davis .................... 424/49 |
| 4,138,383 | 2/1979 | Rembaum et al. .................. 424/9 |
| 4,155,870 | 5/1979 | Jurgensen .................... 252/131 |
| 4,259,103 | 3/1981 | Malek et al. .................. 71/67 |
| 4,324,630 | 4/1982 | Sugita et al. .................. 204/192 |
| 4,339,429 | 7/1982 | Raaf et al. .................... 424/49 |
| 4,348,378 | 9/1982 | Kosti .................... 424/49 |
| 4,433,959 | 2/1984 | Faunce .................... 433/201 |
| 4,502,497 | 3/1985 | Siahou .................... 132/84 |
| 4,516,571 | 5/1985 | Buchan .................... 128/893 |
| 4,585,652 | 4/1986 | Miller et al. .................... 424/83 |
| 4,621,120 | 11/1986 | Hollister .................... 525/327.1 |
| 4,670,185 | 6/1987 | Fujiwara et al. .................... 252/311 |
| 4,761,417 | 8/1988 | Maruko .................... 514/280 |
| 4,780,320 | 10/1988 | Baker . |
| 4,797,234 | 1/1989 | Speaker et al. .................... 264/4.1 |
| 4,802,255 | 2/1989 | Breuer et al. . |
| 4,822,339 | 4/1989 | Tran .................... 604/82 |
| 4,837,007 | 6/1989 | Duckworth et al. .................. 424/52 |
| 4,871,352 | 10/1989 | Tran .................... 604/82 |
| 4,892,736 | 1/1990 | Goodson . |
| 4,904,479 | 2/1990 | Illum .................... 424/9 |
| 4,917,892 | 4/1990 | Speaker et al. .................... 424/401 |
| 4,919,939 | 4/1990 | Baker . |
| 4,941,989 | 7/1990 | Kramer et al. .................... 252/102 |
| 4,959,220 | 9/1990 | Yamamoto et al. .................. 424/54 |
| 4,978,392 | 12/1990 | Jones . |
| 4,980,150 | 12/1990 | Keith . |
| 5,019,723 | 5/1991 | Tran .................... 604/82 |
| 5,036,006 | 7/1991 | Sanford et al. .................... 424/3 |
| 5,037,818 | 8/1991 | Sime .................... 514/183 |
| 5,064,613 | 11/1991 | Higgs et al. .................... 422/16 |
| 5,154,932 | 10/1992 | Burba et al. .................... 424/605 |
| 5,185,155 | 2/1993 | Behan et al. .................... 424/451 |
| 5,211,939 | 5/1993 | Turesky et al. .................... 424/49 |
| 5,238,749 | 8/1993 | Cueman et al. .................... 428/441 |
| 5,240,710 | 8/1993 | Bar-Shalom et al. ................ 424/422 |
| 5,250,288 | 10/1993 | Turesky et al. .................... 424/49 |

FOREIGN PATENT DOCUMENTS

| | | |
|---|---|---|
| 0079400 | 5/1983 | European Pat. Off. . |
| 244118 | 11/1987 | European Pat. Off. .............. 424/54 |
| WO90/10400 | 9/1990 | PCT Int'l Appl. . |

Primary Examiner—Shep K. Rose
Attorney, Agent, or Firm—Fish & Richardson

[57] ABSTRACT

An anti-microbial composition includes particles having an outer surface onto which an anti-microbial agent has been adsorbed. The particles can be used, for example, for coating the bristles of toothbrushes.

21 Claims, No Drawings

POLYMERIC PARTICLES FOR DENTAL APPLICATIONS

This is a continuation of application Ser. No. 07/759,535, filed Sep. 13, 1991, now abandoned.

BACKGROUND OF THE INVENTION

The invention relates to particles having an anti-microbial agent adsorbed on their surface.

Most humans suffer from tooth decay and periodontal disease caused by bacteria in the mouth. As a result, decreasing the number of bacteria in the mouth has long been the target of persons working in the health care field. The most common way of minimizing the number of bacteria is to brush and floss the teeth regularly, and to visit a dental hygienist to have the teeth and gums cleaned thoroughly. Another prior approach to control bacteria in the mouth is to rinse with a solution containing a known anti-microbial agent like chlorhexidine digluconate.

One of the major side effects of rinsing with a chlorhexidine solution is a yellow-brown stain which develops on teeth, tongue, and fillings. Although this stain can be professionally removed, it is not cosmetically pleasing. In addition to the staining, taste disturbances in the perception of sweet and salt may develop, and in a few persons, scaling and soreness of the oral mucosa. The main reason for these side effects is the high concentration of chlorhexidine or salt thereof used in the rinse.

After a toothbrush has been used, there are a large number of bacteria clinging to the bristles, even after the brush has been rinsed. This, of course, is undesirable, and these bacteria typically will multiply on the bristles between uses. To counter this problem, various approaches to making self-sterilizing toothbrushes have been described in the art.

SUMMARY OF THE INVENTION

In one aspect, the invention features a toothbrush which has bristles coated with solid particles onto which an anti-microbial agent (e.g., chlorhexidine) has been adsorbed. The particles are released from the bristles during brushing and contact the surface of the mouth, teeth, and gums, clinging to the surface and providing good anti-microbial action at relatively low concentration, thus limiting the side effects of chlorhexidine. Moreover, the particles make the toothbrush self-sterilizing because they inhibit the growth of bacteria on the bristles between uses.

The preferred particles are polymers such as polystyrene microspheres having an average diameter of between $0.05\mu$ and $1\mu$, more preferably between $0.3\mu$ and $1\mu$. Other types of organic polymeric particles that can be used include polyvinyltoluene and methacrylate-styrene copolymers.

The preferred particles have an ionic charge; the preferred anti-microbial agents have an ionic charge opposite that of the preferred particles. The preferred anti-microbial agent, chlorhexidine, is positively charged; the outer surface of the preferred polystyrene microspheres has a negative charge.

Other aspects of the invention feature compositions comprising the particles bearing the adsorbed anti-microbial. One featured composition includes particles in which the anti-microbial agent is adsorbed only on the outer surface of the particle; adsorbing the agent only on the outer surface fosters efficient use of the agent. Another featured composition includes particles having a diameter of between $0.01\mu$ and $10\mu$. These compositions can be included on the bristles of toothbrushes, in toothpaste, in oral rinses, and in dental floss.

Another aspect of the invention features a wear-indicating toothbrush. The bristles of the toothbrush include colored particles that release when the toothbrush is used, resulting in a loss of color in the bristles of the toothbrush and providing an indication of the degree of wear of the bristles.

Coated bristles, as used herein, means that at least two or more of the filaments that make up the bristles of a typical toothbrush have a relatively even distribution of the particles on a portion of their surface. Coated does not mean to imply that the surface portion is entirely covered with the particles.

Microspheres, as used herein, are particles that are generally spherical.

Diameter, as used herein, means the average diameter of the particle.

Other features and advantages of the invention will be apparent from the description of the preferred embodiment thereof, and from the claims.

DESCRIPTION OF THE PREFERRED EMBODIMENT

The preferred particles are polystyrene microspheres with a charged surface onto which chlorhexidine has been adsorbed. The particles preferably are included in the bristles of toothbrushes.

The polystyrene microspheres are available from a number of sources, e.g., Interfacial Dynamics Corp. of Portland, Oreg., packaged as a 5.41 percent w/w suspension in distilled water. The microspheres are carboxylate-modified, hydrophilic latexes of high negative surface charge density. The microspheres preferably have an average diameter of less than $1\mu$, and greater than $0.05\mu$, more preferably $0.3\mu$. Microspheres having too great an average diameter will provide too low a dosage of chlorhexidine. The most preferred microspheres for use in toothbrushes have an average diameter of $0.865\mu$. The general methodology used to produce the preferred polystyrene microspheres is well-known and is described, for example, in Chung-li et al., Progress in Colloid and Polymer Science, Vol. 60, pp. 163-175 (1976); Goodwin et al., Journal of Colloid and Polymer Science, Vol. 252, p. 464 (1974); Goodwin et al., British Polymer Journal, Vol. 5, p. 347 (1973).

The chlorhexidine gluconate can be purchased as a 20 percent w/w aqueous solution from a number of sources, e.g., Pliva Pharmaceutical of Zagreb, Yugoslavia and ICI Ltd. of England. Chlorhexidine contains two positively-charged biguanide groups; gluconate is the counter-ion.

The preferred chlorhexidine-treated particles were made by first preparing a 500 mg/ml chlorhexidine gluconate solution with water. The solution has a resultant pH of a little less than 7.0; NaOH was added to increase the pH to 9. A portion (39.6 ml) of the chlorhexidine solution was transferred to a 50 ml centrifuge tube, 0.4 ml of a polystyrene microsphere suspension (Cat. No. 10-36-23 from Interfacial Dynamics Corp.; 5.41% w/w) added to make a final concentration of 0.54 mg/ml, and the mixture shaken gently to avoid foaming. The tubes are then placed in a shaker water bath (80 rpm) at 40° C. for one hour, following which the dispersions are centrifuged at 3050 rpm for 30 minutes to separate the treated particles. The supernatant is carefully removed by syringe. The particles are redispersed in 40 ml of water, and centrifuged for 45 minutes at 3050 rpm. The supernatant is again carefully removed (to avoid disturbing the particles), and redispersed in 50 ml of water for storage.

Scanning electron micrographs (35,000×) of the particles prior to chlorhexidine treatment show a smooth surface, while the treated particles appear to have random bumps of precipitated material on the surface.

The pH of the chlorhexidine solution affects the amount of adsorption. The surface of the particle is stable in the pH range of 7-9; however, because the chlorhexidine molecule has two biguanide groups (pKa 2.2 and 10.3), the population of chlorhexidine molecules is gradually shifting to less charge as the pH of the solution increases. With less charge, the molecules can pack closer together on the surface, and thus more chlorhexidine will be adsorbed.

It is preferred that as much chlorhexidine as possible should be adsorbed onto the surface of the microspheres. With the prefered particles the amount of chlorhexidine adsorbed exceeded 100 ug of chlorhexidine per mg of microspheres.

Toothbrushes having bristles coated with the particles were prepared by first placing 300 ml of chlorhexidine-treated particle dispersion into a polystyrene beaker. Ten toothbrushes (P-35, sold by Oral-B Laboratories of Redwood City, Calif.) were inserted into a circular formation of holes in a styrofoam holder, with the bristles facing inward; the toothbrushes are secured by encircling their handles with tape. The holder was mounted as a stirring shaft, with the brush heads beneath the propeller. The assembly was lowered into the dispersion sufficiently that the brush heads and propeller were immersed. The dispersion was stirred at 150 rpm for 24 hours. The beaker containing the dispersion was removed, and replaced with a fresh beaker containing 300 ml of distilled water. The brushes were rinsed for five minutes at 150 rpm; the rinse procedure was then repeated with a fresh beaker of water. The toothbrushes were removed and placed in an oven at 67° C. to dry, and then stored in a 65 percent relative humidity cabinet at room temperature.

During the above procedure, the chlorhexidine-treated particles coat the nylon filaments of the toothbrushes. The total loading of particles onto each toothbrush, determined by chloroform extraction of the bristles, was 0.87 mg. A photograph of a bristle (3,000× magnification) showed a relatively uniform coating of the particles on the filaments.

When used, the toothbrushes release the particles in the mouth, and the particles release chlorhexidine, which inhibits bacteria. Only a portion of the particles are released from the bristles each time brushing occurs, and as a result the toothbrush provides a low-dosage of chlorhexidine over the course of many uses before the supply of microspheres on the bristles has been used up. Moreover, it is believed that the particles released from the bristles cling to the interior of the mouth after brushing, slowly releasing chlorhexidine and fighting bacterial growth even after brushing is complete. The bristles themselves, because they retain a portion of the particles after brushing, are self-sterilizing.

OTHER EMBODIMENTS

Other embodiments are within the following claims. For example, anti-microbial agents suitable for adsorption onto particles include other bisbiguanides such as alexidine, which has a positive charge; bispyridines such as octenidine (positive charge); pyrimidines such as hexetidine (positive charge); quaternary ammonium ions such as cetylpyridinium, domiphen, benzalkonium, and benzethonium (all positively charged); alkaloids such as sanguinarine (positive charge); heavy metal ions such as zinc, stannous, and copper (all positively charged); surfactants such as lauryl sulfate, lauryl sarcosinate, and deoxycholate (all negatively charged); phenolic compounds such as eucalyptol, hexylresorcinol, menthol, methylsalicylate, phenol, 2-phenylphenol, and thymol; antibiotics such as erythromycin, kanamycin, metronidazole, niddamycin, spyramycin, and tetracycline; and enzymes such as amyloglucosidase, glucose oxidase, and mutanase, which include both positive and negative charges. Of course, other salts of chlorhexidine (e.g., the diacetate) can be used instead of the digluconate. Preferably the agent should be charged (cationic or anionic), and the particle should be selected so that its surface charge is opposite the charge of the agent. Other examples of suitable charged particles include polystyrene microspheres with a positively-charged surface (also available from Interfacial Dynamics Corp.); particles made from polyvinyltoluene with negatively-charged sulfate groups; particles made from methacrylate-styrene copolymer with a positively or negatively charged surface; and silica particles, which have a negative charge. Other inorganic particles that can be used include carbon (negative charge); chromium hydroxide (positive or negative charge); clay (negative charge); hydroxyapatite (positive or negative charge); iron oxide (positive or negative charge); mica (negative charge); silica (negative charge); and titanium dioxide (negative charge). Other organic particles that can be used include polymers like polymethyl methacrylate (slight negative charge); and carboxymethylcellulose (negative charge); and copolymers like styrene/methacrylate or other acrylic esters (slight negative charge), styrene/2-vinylpyridine (positive charge), and tetrafluoroethylene/propylene (negative charge). The particles should be between $0.01\mu$ and $10\mu$ in size, and an anti-microbial agent having an opposite charge to that of the particle can be adsorbed onto the surface of the particles by an analogous procedure to the preferred example.

The particles apparently do not need to have the opposite charge of the anti-microbial agent for adsorption to occur. Positively-charged polystyrene particles (Cat. No. 20-107-3 from Interfacial Dynamics Corp.) treated with chlorhexidine digluconate following the same general procedure previously described resulted in some adsorption of chlorhexidine onto the surface of the particles.

The particles can be used in other applications besides toothbrushes. For example, dental floss can be coated or impregnated with the particles by a procedure similar to that described above for toothbrushes. Moreover, the particles can be used in either toothpaste or mouthwash. For example, the dispersion obtained after the chlorhexidine was adsorbed on the surface of the polystyrene microspheres can be used as a mouthwash. Of course, the other ingredients of the toothpaste or mouthwash should be ionically compatible with the particles and anti-microbial agent; thus, if chlorhexidine is used as the agent a negatively charged surfactant should not be included in the composition. More preferably, the toothpaste or mouthwash should include only non-ionic surfactants. Additionally, the bristles of the toothbrush can be made of polyester as opposed to nylon filament.

The particles are available in colored forms. The particles can be colored with various dyes, which can be non-fluorescent, fluorescent, polychromatic (different fluorescent colors depending on the light wavelength), or chemiluminescent (light emitted in the presence of a chemical). Examples of non-fluorescent dye coated particles include red, yellow, and blue polystyrene microspheres (with negatively-charged sulfate, carboxyl, or carboxylate-modified surface groups) available from Interfacial Dynamics Corp. of Portland, Oreg.; the yellow, red, blue, and violet polystyrene and carboxylate-modified polystyrene microspheres available from Polysciences, Inc. of Warrington, Pa.; and yellow, red, blue, brown, and black polymethyl methacrylate microspheres. Examples of fluorescent-dye coated particles include polystyrene microspheres with amidine, carboxyl, sulfate, carboxylate-modified, or aldehyde-modified surface groups available from the above suppliers. Polychromatic and chemiluminescent particles are also available from Polysciences.

The colored particles—with or without an anti-microbial agent adsorbed—can be coated onto the bristles of toothbrushes by the procedures described above. The particles provide color to the bristles which diminish as the brush is used and the particles are released. The loss of color is indicative of the amount of wear on the brush and, if an agent is bound to the particle, the loss of bacteria fighting power.

A wear-indicating toothbrush was prepared as follows. Blue-dyed carboxylate-modified polystyrene microspheres (0.98$\mu$) were obtained from Polysciences, Inc. They were treated with chlorhexidine according to the procedure previously described, except the chlorhexidine solution had a concentration of 100 ug/ml. The mean chlorhexidine (CHG) adsorption was 93±3 ug CHG/mg latex, or 1.60±0.05 ug CHG/cm$^2$, which is slightly less than that obtained for the standard undyed particles (130+20 ug CHG/mg latex or 1.98±0.30 ug CHG/cm$^2$). Oral-B P-35 brushes were coated with the CHG-treated blue particles by the procedure described above. The coated brushes appeared blue. A few were tested on the toothbrush wear machine to 5,000 revolutions in water, which would represent about two months of home brushing. The worn brushes lost blue particles from about three-fourths of the bristle length. The remaining particles appeared concentrated in the bristle region near the base of the brush. Thus, the use of blue particles serves as a visible indicator to the consumer both of the level of wear on the toothbrush, and of when the antimicrobial is depleted.

I claim:

1. An anti-microbial composition for oral hygiene, comprising a toothpaste or a mouthwash including solid particles having an ionically charged outer surface onto which an anti-microbial agent having an ionic charge that is the opposite of the ionic charge of said outer surface has been adsorbed, wherein said anti-microbial agent is present in said composition only on said outer surface.

2. The composition of claim 1 wherein said anti-microbial agent comprises chlorhexidine.

3. The composition of claim 2 wherein said particles comprise polystyrene.

4. The composition of claim 1 wherein said particles are between 0.01$\mu$ and 10$\mu$ in diameter.

5. The composition of claim 4 wherein said particles are between 0.05$\mu$ and 1$\mu$ in diameter.

6. The composition of claim 1 wherein said outer surface is negatively charged layer.

7. The composition of claim 1 wherein said particles comprise organic polymers.

8. Toothpaste comprising the composition of claim 1.

9. The composition of claim 1 wherein said composition comprises an oral rinse.

10. An anti-microbial composition for oral hygiene, comprising a toothpaste or a mouthwash including water insoluble polymeric microspheres having an ionically charged outer surfaces on which an anti-microbial agent having an ionic charge that is the opposite of the ionic charge of said outer surface has been adsorbed.

11. The anti-microbial composition of claim 10 wherein said anti-microbial agent comprises chlorhexidine.

12. The anti-microbial composition of claim 10 wherein said microspheres comprises polystyrene.

13. The anti-microbial composition of claim 10, wherein said outer surface is negatively charged.

14. The anti-microbial composition of claim 10 wherein said microspheres have a diameter of between 0.01$\mu$ and 10$\mu$.

15. The composition of claim 1 wherein said composition comprises an oral rinse.

16. The composition of claim 10 wherein said composition comprises a toothpaste.

17. A method of inhibiting bacteria in the mouth comprising
adsorbing an ionically charged anti-microbial agent onto only the outer surface of a polymeric particle, said outer surface having the opposite ionic charge of said anti-microbial agent;
incorporating said polymeric particle with said anti-microbial agent adsorbed onto its outer surface into a toothpaste or a mouthwash; and
placing said toothpaste or mouthwash into the mouth of a person to inhibit bacteria in said mouth.

18. The method of claim 17 wherein said anti-microbial agent is chlorhexidine.

19. The method of claim 17 wherein said particles are polystyrene microspheres.

20. The method of claim 17 wherein said polymeric particle is incorporated into an oral rinse.

21. The method of claim 17 wherein said polymeric particle is incorporated into a toothpaste.

* * * * *